United States Patent [19]

Johnson et al.

[11] 4,145,812
[45] Mar. 27, 1979

[54] ADJUSTABLE DENTAL IMPRESSION TRAY

[76] Inventors: James F. Johnson, Rte. 3, Box 1446, Plaquemine, La. 70764; Victor T. Nicholson, 4529 N. Blvd., Baton Rouge, La. 70806

[21] Appl. No.: 842,034

[22] Filed: Oct. 14, 1977

[51] Int. Cl.$^2$ ............................................. A61C 9/00
[52] U.S. Cl. ..................................................... 32/17
[58] Field of Search ....................................... 32/17, 18

[56] References Cited

U.S. PATENT DOCUMENTS

| 310,407 | 1/1885 | Garner | 32/17 |
|---|---|---|---|
| 583,848 | 6/1897 | Dunlap | 32/17 |
| 1,257,947 | 2/1918 | Sternberg | 32/17 |
| 2,426,388 | 8/1947 | Chartrand | 32/17 |
| 3,890,711 | 6/1975 | Burns | 32/17 |

FOREIGN PATENT DOCUMENTS 91790  3/1923  Austria ........................................ 32/17

Primary Examiner—Louis G. Mancene
Assistant Examiner—John J. Wilson
Attorney, Agent, or Firm—David L. Ray; Edgar E. Spielman, Jr.

[57] ABSTRACT

An adjustable dental impression tray including a primary unit and two complementary movable units slidably mounted telescopically on the primary unit for adjustment with respect thereto. The primary unit is provided with an outwardly extending flexible flap cooperable with a rigid tab and is adapted to receive and secure the movable unit in a predetermined adjusted position with respect to the primary unit.

10 Claims, 5 Drawing Figures

ADJUSTABLE DENTAL IMPRESSION TRAY

BACKGROUND OF THE INVENTION

This invention relates generally to new and useful improvements of dental impression trays, and particularly seeks to provide a novel dental impression tray in which adjustments thereof may readily be effected.

Adjustable dental trays have been known for many years. U.S. Pat. No. 3,890,791 issued June 24, 1975, discloses an adjustable dental impression tray including a primary unit and a complementary movable unit slidably mounted telescopically on the primary unit, the primary unit being provided with a T-slot disposed in registry with a complementary slot in the movable unit and a threaded securing device.

However, the above patent does not supply the simplicity of construction and the rigidity, control and locking of the relatively adjustable parts as effected by the inventive construction disclosed herein. The present invention is believed to have several advantages over the prior art which will become more apparent by referring to the following disclosure.

DESCRIPTION OF THE PREFERRED EMBODIMENT

Figure 1:
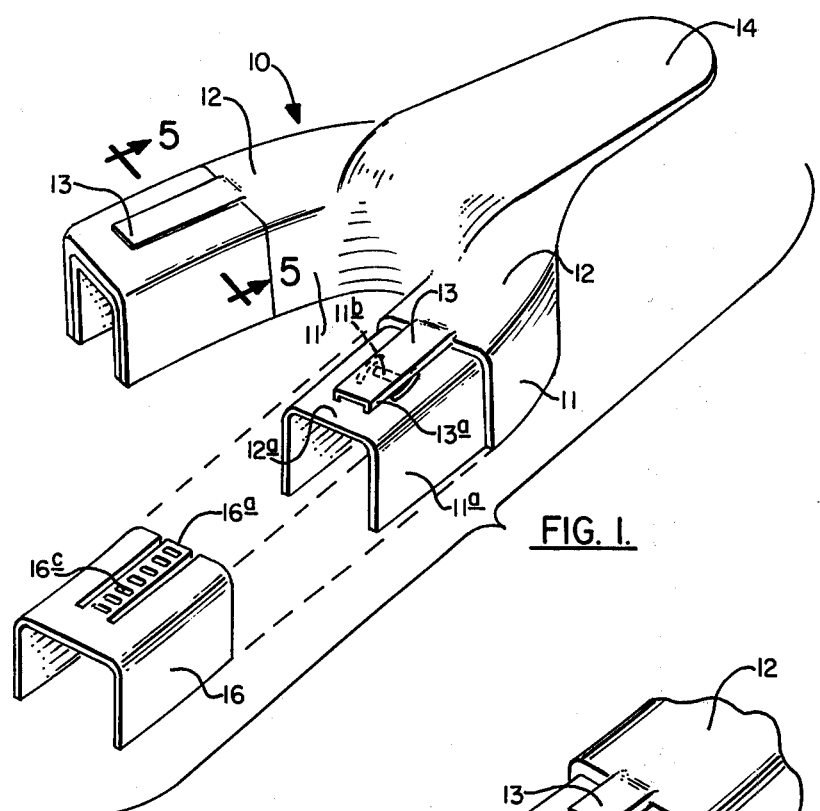
FIG. 1 is an exploded, isometric view of an adjustable dental impression tray constructed in accordance with the invention.
Figure 2:
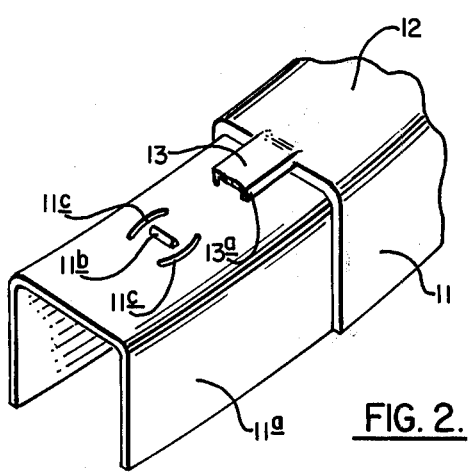
FIG. 2 is an enlarged, partly cut-away view of a portion of the dental impression tray of the present invention.
Figure 3:
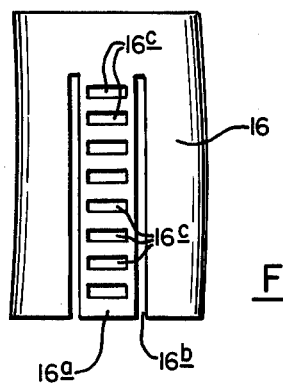
FIG. 3 is a top plan view of the movable unit of the dental impression tray of the present invention.
Figure 4:
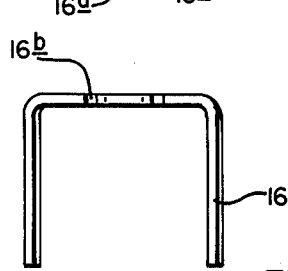
FIG. 4 is an end view of the movable unit of the adjustable dental impression tray of the present invention.

Referring now to the drawings, the dental impression tray of the present invention can be seen in FIG. 1 to include a primary unit generally indicated by the numeral 10, and a movable extension unit, generally indicated by the numeral 16. The primary unit can be seen to include a handle 14 for grasping by the user and two U-shaped primary legs 11 extending outwardly from the handle.

Extending from legs 11 are secondary legs 11a. Secondary legs 11a are generally U-shaped as are primary legs 11, but are slightly smaller in cross-sectional dimensions. Both legs 11 and 11a have two generally vertical sidewalls connected by top walls 12 and 12a to form a U-shaped channel.

Top wall 12a has a tab 11b therein which extends vertically upward from the top wall of channel 11a. Furthermore, leg 11a has two slots 11c therein which permit tab 11b to easily flex upwardly and downwardly.

Extending outwardly from leg 11 over tab 11b is a flexible U-shaped flap 13 which has vertical sidewalls 13a thereon. Flap 13 extends outwardly over tab 11b approximately the same length as the length of leg 11a.

The movable unit 16 is shown in FIG. 1 to have a generally U-shaped cross-section and to have approximately the same length as leg 11a. Movable unit 16 is dimensioned to nest or telescope snugly over leg 11a. Movable unit 16 has a slotted flap 16a having holes or slots 16c therein and two channels 16b running along the edge of flap 16a. Flap 16a is sized to nest comfortably within flap 13, the edges 13a of flap 13 being received within slot 16b of movable unit 16, and tab 11b being received within slots 16c.

Figure 5:
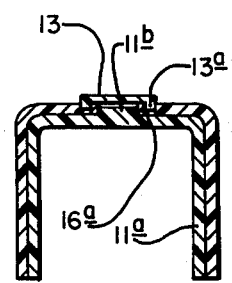
FIG. 5 is a cross-sectional view taken along section lines 5—5 of FIG. 1.

It can thus be seen that when movable unit 16 is aligned with leg 11a and forced thereover, flap 16a fits inside walls 13a of flap 13 and contacts tab 11b. As movable unit 16 is forced farther onto leg 11a, flap 16a is forced upwardly thereby forcing flap 13 upwardly. Tab 11b can then engage each one of the slots 16c individually to hold movable unit 16 in any desired position extending outwardly from primary unit 10. This position is illustrated in FIG. 5 wherein flap 13 is seen to be forced upwardly by flap 16a, flap 16a being fitted over tab 11b. Flap 13 holds flap 16a downwardly on tab 11b.

The dental impression tray of the present invention can be made from any well known material. Preferably a plastic material such as a thermoplastic or thermosetting resin is employed. It can be seen that the dental impression tray of the present invention can be easily molded from a plastic composition and will contain only three molded pieces, two of the three molded pieces being identical. Thus manufacture of the dental tray of the present invention is very inexpensive.

It will be understood that although the above-described embodiments of the invention are directed to trays for taking full arch dental impressions, the principles of the invention are equally adaptable for trays to be used for taking of quadrant, anterior, edentulus. Furthermore it is to be understood that variations and arrangements in proportions and parts may be made within the scope of the appended claims.

What is claimed is:

1. An adjustable dental impression tray including a primary impression unit, a movable extension unit telescopically mounted on said primary unit for adjustment relative thereto, and releasable means for securing said primary and said extension units in their adjusted positions, said primary unit being provided with primary leg portions having secondary leg portions extending therefrom, said primary leg portions having first flap means extending outwardly therefrom and over said secondary leg portions, said secondary leg portions having tab means cooperable with said first flap means, said first flap means being movable relative to said tab means, said movable extension unit being provided with second flap means having a series of slot means therein for registry with said tab means.

2. The tray of claim 1 wherein said primary leg portions and said secondary leg portions are U-shaped in cross-section.

3. The tray of claim 1 wherein said secondary leg portions have slot means adjacent to said tab means to permit said tab means to flex upwardly and downwardly.

4. The tray of claim 1 wherein said first flap means and said second flap means flex upwardly and downwardly.

5. The tray of claim 1 wherein said tab means are aligned with said first flap means.

6. The tray of claim 5 wherein said tab means comprises a protuberance extending upwardly from said secondary leg portions toward said first flap means.

7. The tray of claim 1 wherein said movable extension unit has longitudinal slot means therein for receiving sidewall means formed on said first flap means.

8. The tray of claim 7 wherein said first flap means and said second flap means flex upwardly and downwardly.

9. The tray of claim 8 wherein said tab means are aligned with said first flap means.

10. The tray of claim 9 wherein said tab means comprises a protuberance extending upwardly from said secondary leg portions towards said first flap means.

* * * * *